(12) United States Patent
Lee et al.

(10) Patent No.: US 12,051,504 B2
(45) Date of Patent: Jul. 30, 2024

(54) TWO-PHASE DISEASE DIAGNOSIS SYSTEM AND METHOD THEREOF

(71) Applicant: DEEP BIO INC., Seoul (KR)

(72) Inventors: Sanghun Lee, Seoul (KR); Joonyoung Cho, Seoul (KR); Sun Woo Kim, Seongnam-si (KR)

(73) Assignee: DEEP BIO INC., Seoul (KR)

( * ) Notice: Subject to any disclaimer, the term of this patent is extended or adjusted under 35 U.S.C. 154(b) by 699 days.

(21) Appl. No.: 15/734,907

(22) PCT Filed: Jun. 4, 2019

(86) PCT No.: PCT/KR2019/006759
§ 371 (c)(1),
(2) Date: Dec. 3, 2020

(87) PCT Pub. No.: WO2019/235828
PCT Pub. Date: Dec. 12, 2019

(65) Prior Publication Data
US 2021/0304889 A1    Sep. 30, 2021

(30) Foreign Application Priority Data
Jun. 4, 2018    (KR) .................. 10-2018-0064332

(51) Int. Cl.
*G06T 7/73*    (2017.01)
*G06F 18/23*    (2023.01)
(Continued)

(52) U.S. Cl.
CPC .............. *G16H 50/20* (2018.01); *G06F 18/23* (2023.01); *G06N 3/042* (2023.01); *G06N 3/08* (2013.01); *G06T 7/74* (2017.01); *G16H 30/40* (2018.01)

(58) Field of Classification Search
CPC ........ G16H 50/20; G16H 30/40; G16H 10/40; G06F 18/23; G06N 3/042; G06N 3/08;
(Continued)

(56) References Cited

U.S. PATENT DOCUMENTS 9,836,839 B2    12/2017    Champlin et al.
10,133,938 B2   11/2018    Kim et al.
(Continued)

FOREIGN PATENT DOCUMENTS

CN    107909102          4/2018
JP    2013500464    *   1/2013    .......... A61B 5/0062
(Continued)

OTHER PUBLICATIONS

Angel Cruz-Roa et al. "High-throughput adaptive sampling for whole-slide histopathology image analysis (HASHI) via convolutional neural networks: Application to invasive breast cancer detection", https://doi.org/10.1371/journal.pone.0196828, May 24, 2018, pp. 1-23.

(Continued)

*Primary Examiner* — Jerome Grant, II
(74) *Attorney, Agent, or Firm* — PnK IP LLC

(57) ABSTRACT

A two-phase disease diagnosis system includes a processor and a storage device storing a neural network, and using a slide including a biometric image and the neural network. The system includes a patch neural network that receives, through an input layer, a given patch segmented in a given size from the slide and outputs patch level diagnosis results indicating whether a disease is present in the patch and a slide diagnosis engine that marks a patch determined to be cancer based on the patch level diagnosis results for each of multiple patches included in the slide and outputs slide level diagnosis results indicating whether a disease is present in the slide based on the marked results. The patch neural (Continued)

network receives, through the input layer, four-channel information including original color information three-channels and a gray channel for the patch.

12 Claims, 9 Drawing Sheets

(51) Int. Cl.
  *G06N 3/042* (2023.01)
  *G06N 3/08* (2023.01)
  *G16H 30/40* (2018.01)
  *G16H 50/20* (2018.01)

(58) Field of Classification Search
  CPC .......... G06N 3/045; G06N 7/01; G06N 20/00; G06T 7/74
  USPC ........................................................ 382/128
  See application file for complete search history.

(56) References Cited

U.S. PATENT DOCUMENTS

| 10,417,525 | B2 | 9/2019 | Ji et al. |
| 2016/0086078 | A1 | 3/2016 | Ji et al. |
| 2016/0350914 | A1 | 12/2016 | Champlin et al. |
| 2017/0083772 | A1 | 3/2017 | Kim et al. |
| 2017/0161545 | A1 | 6/2017 | Champlin et al. |
| 2017/0169313 | A1 | 6/2017 | Choi et al. |
| 2018/0068426 | A1 | 3/2018 | Matsunaga |
| 2018/0114317 | A1 | 4/2018 | Song et al. |
| 2019/0120845 | A1* | 4/2019 | Remark ................ G01N 33/53 |
| 2019/0385306 | A1 | 12/2019 | Kim |
| 2019/0392253 | A1 | 12/2019 | Ji et al. |

FOREIGN PATENT DOCUMENTS

| KR | 10-2016-0034814 | 3/2016 | |
| KR | 10-2017-0034226 | 3/2017 | |
| KR | 10-2017-0070715 | 6/2017 | |
| KR | 10-2018-0021635 | 3/2018 | |
| KR | 10-2018-0066983 | 6/2018 | |
| WO | 2016/191462 | 12/2016 | |
| WO | WO2019146066 | * 8/2019 | ....... A61B 1/000094 |

OTHER PUBLICATIONS

International Search Report dated Oct. 7, 2019, issued in International Application No. PCT/KR2019/006759 (with English Translation).
Jamaluddin, et al., "Tumor detection and whole slide classification of H&E lymph node image using convolutional neural network", IEEE ICSIPA, Sep. 12, 2017 (Year: 2017).
Wang, et al., "Deep Learning for Identifying Metastatic Breast Cancer", Jun. 18, 2016 (Year: 2016).

* cited by examiner

|  | accuracy | precision= PPV | sensitiviey= recall | specificity |
|---|---|---|---|---|
| train (62358:108300) | 0.9913 | 0.9957 | 0.9805 | 0.9975 |
| val (8963:15499) | 0.9825 | 0.9965 | 0.9556 | 0.9981 |
| test (14898:19089) | 0.9770 | 0.9891 | 0.9582 | 0.9917 |

FIG. 9

|  | accuracy | precision= PPV | sensitiviey= recall | specificity |
|---|---|---|---|---|
| train (478:218) | 0.9296 | 0.9447 | 0.9545 | 0.8732 |
| val (117:57) | 0.9368 | 0.9550 | 0.9464 | 0.9194 |
| test (1302:1658) | 0.9213 | 0.9199 | 0.8994 | 0.9385 |

TWO-PHASE DISEASE DIAGNOSIS SYSTEM AND METHOD THEREOF

CROSS-REFERENCE TO RELATED APPLICATION

This application is a National Stage Entry of International Application No. PCT/KR2019/006759, filed on Jun. 4, 2019, and claims priority from and the benefit of Korean Patent Application No. 10-2018-0064332, filed on Jun. 4, 2018, each of which is hereby incorporated by reference for all purposes as if fully set forth herein

BACKGROUND

Field

The invention relates to a disease diagnosis system using a neural network and a method thereof and, more particularly, to a system capable of diagnosing a given disease (e.g., prostate cancer) when an image of a biometric tissue is input using a neural network trained by performing learning through the neural network and a method thereof.

Discussion of the Background

One of important tasks performed in pathology or a pathology department is to perform diagnosis for determining a state or symptom of a specific disease by reading a biometric image of a patient. Such diagnosis is a method dependent on experiences and knowledge of a long experienced healthcare worker.

With the recent development of machine learning, attempts to automate a task of recognizing or classifying an image using a computer system are actively made. In particular, attempts to automate diagnosis, performed by an experienced healthcare worker, using a neural network (e.g., a deep learning method using a convolutional neural network (CNN)), that is, a kind of machine learning, are sought.

In particular, in diagnosis through deep learning using a neural network (e.g., CNN), a feature of a disease factor not known to an experienced healthcare worker is found out in that experiences and knowledge of an experienced healthcare worker are not simply automated as in a prior art, but a desired answer is derived by autonomously finding feature elements through learning.

In general, a piece, that is, a patch (or called), of a biometric image used for the diagnosis of a disease through a neural network using a biometric image. That is, an experienced healthcare worker annotates or labels a state of a specific disease (e.g., whether cancer has been revealed) with respect to a corresponding patch, and trains a neural network using a plurality of such annotated patches as training data. In this case, a convolutional neural network may be used as the neural network.

However, in such a method, a trained neural network determines a state of a disease of a corresponding patch based on only an image characteristic of the corresponding patch. When a state of a specific biometric tissue is actually determined with respect to a specific disease, not only the specific biometric tissue itself, but the present condition whether a shape or a specific pattern is present) of a surrounding tissue of the specific biometric tissue has to be considered. However, there is a problem in that a conventional method is not suitable for such a case.

Meanwhile, in conventional learning, a biometric image or a color of a patch itself is input as input data. That is, in general, input data defined as three channel values of red-green-blue (RGB) is used without any change.

However, in such a case, a color of a dyed tissue may be different depending on characteristics of a dying reagent used for the dyeing of a biometric tissue corresponding to a biometric image. This may have a direct influence on a trained neural network.

Accordingly, it may be preferable to train the neural network using a method that is more robust against a non-fundamental color characteristic according to dyeing, not such a fundamental image characteristic of a tissue.

Furthermore, if whether a disease is revealed is determined for each patch based on diagnosis results of a patch unit, diagnosis results indicating that a disease has been revealed in a specific patch may be output, but there may be a possibility that a disease has not been revealed in a wider range.

Accordingly, it may be preferable to separately determine whether a disease has been revealed in the entire slide including a corresponding patch based on diagnosis results for each patch.

The above information disclosed in this Background section is only for understanding of the background of the inventive concepts, and, therefore, it may contain information that does not constitute prior art.

SUMMARY

The exemplary embodiments provide a diagnosis system using a neural network, which can further increase accuracy using not only a specific patch, but a surrounding patch for learning in order to determine a state of a disease (e.g., whether a disease has been revealed or an index indicative of a state of the disease) for a specific patch, and a method thereof.

The exemplary embodiments provide a diagnosis system using a neural network, which can have a characteristic robust against a color not a fundamental image characteristic in diagnosing whether a disease has been revealed, and a method thereof.

Furthermore, The exemplary embodiments provide a diagnosis system using a neural network, which can effectively perform diagnosis with high accuracy using diagnosis results for each patch in determining whether a disease has been revealed in a wide biometric tissue including a corresponding patch, not the diagnosis results for each patch themselves, and a method thereof.

A two-phase disease diagnosis system includes a processor and a storage device storing a neural network, and using a slide including a biometric image and the neural network. The system includes a patch neural network that receives, through an input layer, a given patch segmented in a given size from the slide and outputs patch level diagnosis results indicating whether a disease is present in the patch and a slide diagnosis engine that marks a patch determined to be cancer based on the patch level diagnosis results for each of multiple patches included in the slide and outputs slide level diagnosis results indicating whether a disease is present in the slide based on the marked results. The patch neural network receives, through the input layer, four-channel information including original color information three-channels and a gray channel for the patch.

The slide diagnosis engine may form a plurality of clusters by clustering patches determined to be cancer using a given method, may receive a plurality of cluster features of each of the formed clusters as an input value, and may output the slide level diagnosis results for the slide including the clusters.

The patch neural network may include a layer which outputs a feature value corresponding to a probability that a disease is to have been revealed in the patch. The patch neural network may output patch level diagnosis results in which a corresponding patch is determined to be cancer when a feature value is a given threshold value or more, and may output a plurality of patch level diagnosis results for one patch based on each of a plurality of the threshold values.

The slide diagnosis engine may form M (M is a natural number equal to or greater than 2) clusters by clustering N (N is a natural number equal to or greater than 2) threshold values and a patch in which a disease has been revealed based on each of the N threshold values using a given method, may calculate P (P is a natural number equal to or greater than 2) cluster features for each of the formed clusters, may receive M×N×P cluster features as at least a value, and may output the slide level diagnosis results for the slide including the clusters.

The cluster feature may include the number of patches, an average of probability values for a possible disease for each patch, a maximum value of probability values for a possible disease for each patch, and a minimum value of probability values for a possible disease for each patch.

The cluster feature may further include a major axis, a minor axis, an area, and density of each of the clusters.

The disease may be prostate cancer.

According to another example, a two-phase disease diagnosis system is implemented in a system, including a processor and a storage device storing a neural network and using a slide which is a biometric image and the neural network. The diagnosis system includes a patch neural network that receives, through an input layer, a given patch segmented in a given size from the slide and outputs patch level diagnosis results indicating whether a disease is present in the patch and a slide diagnosis engine that marks a patch determined to be cancer based on the patch level diagnosis results for each of multiple patches included in the slide and outputs slide level diagnosis results indicating whether a disease is present in the slide based on the marked results. The slide diagnosis engine forms a plurality of clusters by clustering patches determined to be cancer using a given method, receives a plurality of cluster features of each of the formed clusters as an input value, and outputs the slide level diagnosis results for the slide including the clusters.

According to some exemplary embodiments, a disease diagnosis method implemented in a system, including a processor and a storage device storing a neural network, and using a slide which is a biometric image and the neural network includes the steps of receiving, by the system, a given patch segmented in a given size from the slide through an input layer and outputting patch level diagnosis results indicating whether a disease is present in the patch; and marking, by the system, a patch determined to be cancer based on the patch level diagnosis results for each of multiple patches included in the slide and outputs slide level diagnosis results indicating whether a disease is present in the slide based on the marked results. The step of outputting the patch level diagnosis results may include receiving, through the input layer, four-channel information including original color information including three channels and a gray channel for the patch.

The step of outputting the slide level diagnosis results may include the steps of forming, by the system, a plurality of clusters by clustering patches determined to be cancer using a given method and receiving a plurality of cluster features of each of the formed clusters as an input value and outputting the slide level diagnosis results for the slide including the clusters.

The step of outputting the patch level diagnosis results may include, the neural network including a layer which outputs a feature value corresponding to a probability that a disease is to have been revealed in the patch, and a step of outputting patch level diagnosis results for determining a corresponding patch to be cancer when a feature value is a given threshold value or more. A plurality of patch level diagnosis results for one patch may be output based on each of a plurality of the threshold values.

The step of outputting the slide level diagnosis results may include the steps of forming M (M is a natural number equal to or greater than 2) clusters by clustering N (N is a natural equal to or greater than 2) threshold values and a patch for a revealed disease based on each of the N threshold values using a given method, and calculating P (P is a natural number equal to or greater than 2) cluster features for each of the formed clusters, receiving M×N×P cluster features as at least a value, and outputting the slide level diagnosis results for the slide including the clusters.

According to another example, a disease diagnosis method is implemented in a system, including a processor and a storage device storing a neural network, and uses a slide including a biometric image and the neural network. The method includes the steps of receiving, by the system, a given patch segmented in a given size from the slide through an input layer and outputting patch level diagnosis results indicating whether a disease is preset in the patch, and marking, by the system, a patch determined to be cancer based on the patch level diagnosis results for each of multiple patches included in the slide and outputs slide level diagnosis results indicating whether a disease is present in the slide based on the marked results. The step of outputting the slide level diagnosis results may include the step of forming a plurality of clusters by clustering patches determined to be cancer using a given method, receiving a plurality of cluster features of each of the formed clusters as an input value, and outputting the slide level diagnosis results for the slide including the clusters.

The methods may be implemented by a computer program installed on a data processor.

According to some exemplary embodiments, there is an effect in that diagnosis having higher accuracy can be provided by providing a neural network capable of determining a state of a disease for a specific patch with consideration taken of even a macro-patch, further including a surrounding patch in addition to the specific patch, while performing diagnosis on the specific patch.

Furthermore, according to some exemplary embodiments, there are provided a diagnosis system using a neural network, which can have a characteristic robust against a variation attributable to various factors of a color not a fundamental image characteristic, in diagnosing whether a disease has been revealed, while preventing the neglection of an image characteristic indicated due to a color difference and related to the disease, which may occur when only a gray channel is simply used, because not only received input data, that is, original color values (e.g., RGB 3-channel values) of a patch, but the gray channel is additionally used as the input data, and a method thereof.

Furthermore, according to some exemplary embodiments, there is an effect in that diagnosis can be effectively performed with high accuracy because whether a disease has been revealed in a slide including a corresponding patch is determined again using a cluster and features (characteristics) of the cluster in order to solve a problem occurring in determining whether a disease has been revealed in a slide, including a corresponding patch, based on only diagnosis results for each patch themselves.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate exemplary embodiments of the invention, and together with the description serve to explain the inventive concepts.

FIG. 9 is a diagram illustrating experiment results of a slide level diagnosis method according to an exemplary embodiment.

DETAILED DESCRIPTION

Figure 1:
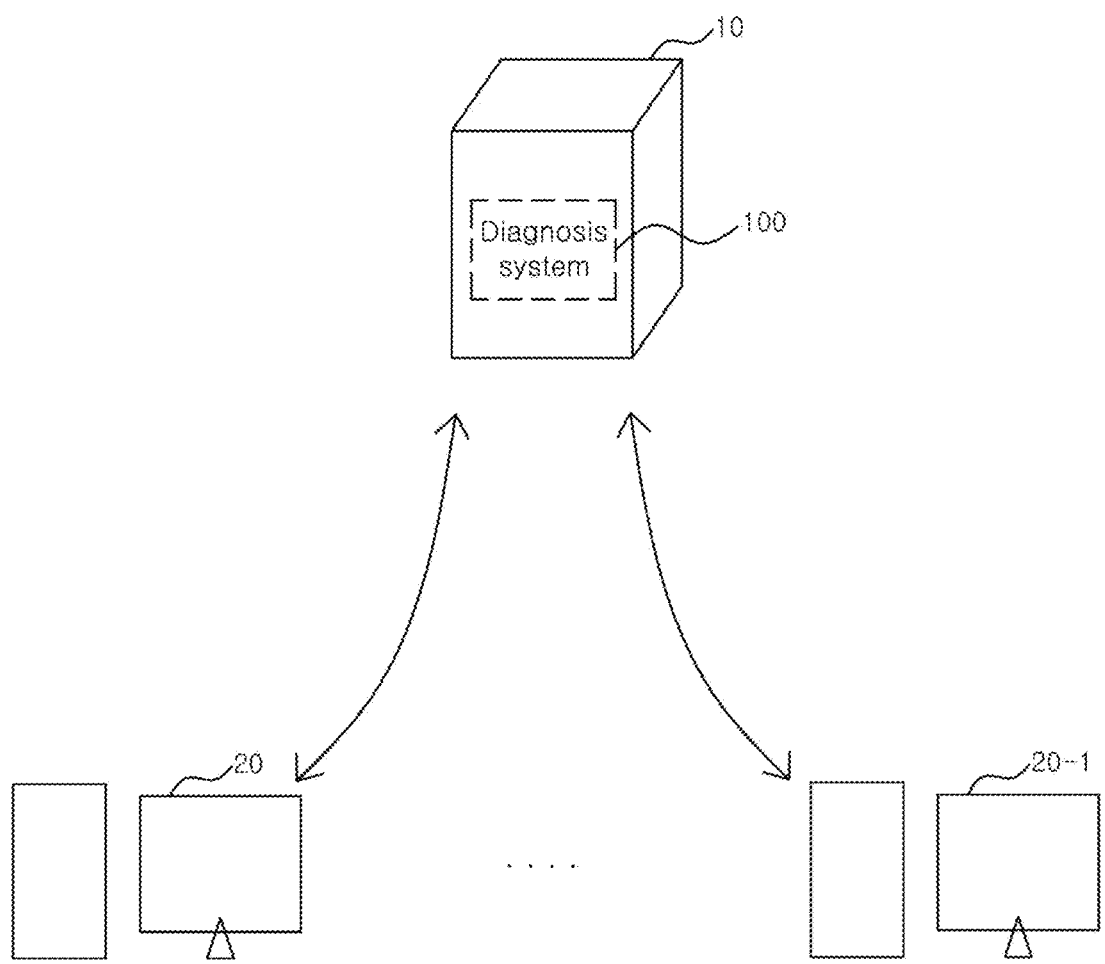
FIG. 1 is a diagram illustrating a schematic system configuration of a disease diagnosis system using a neural network according to an exemplary embodiment.

As customary in the field, some exemplary embodiments are described and illustrated in the accompanying drawings in terms of functional blocks, units, and/or modules. Those skilled in the art will appreciate that these blocks, units, and/or modules are physically implemented by electronic (or optical) circuits, such as logic circuits, discrete components, microprocessors, hard-wired circuits, memory elements, wiring connections, and the like, which may be formed using semiconductor-based fabrication techniques or other manufacturing technologies. In the case of the blocks, units, and/or modules being implemented by microprocessors or other similar hardware, they may be programmed and controlled using software (e.g., microcode) to perform various functions discussed herein and may optionally be driven by firmware and/or software. It is also contemplated that each block, unit, and/or module may be implemented by dedicated hardware, or as a combination of dedicated hardware to perform some functions and a processor (e.g., one or more programmed microprocessors and associated circuitry) to perform other functions. Also, each block, unit, and/or module of some exemplary embodiments may be physically separated into two or more interacting and discrete blocks, units, and/or modules without departing from the scope of the inventive concepts. Further, the blocks, units, and/or modules of some exemplary embodiments may be physically combined into more complex blocks, units, and/or modules without departing from the scope of the inventive concepts.

The invention may be modified in various ways and may have various embodiments. Specific embodiments are to be illustrated in the drawings and are to be described in the detailed description in detail. It is however to be understood that the invention is not intended to be limited to the specific embodiments, but that the invention includes all of modifications, equivalents and/or substitutions which fall within the technological scope of the invention. In describing the invention, a detailed description of the known technologies will be omitted if it is deemed to make the gist of the invention unnecessarily vague.

Terms, such as a first and a second, may be used to describe various elements, but the elements should not be restricted by the terms. The terms are used to only distinguish one element from the other element.

The terms used in this application are used to merely describe specific exemplary embodiments and are not intended to restrict the invention. An expression of the singular number includes an expression of the plural number unless clearly defined otherwise in the context.

In this specification, a term, such as "include or "have", is intended to designate that a characteristic, a number, a step, an operation, an element, or a part described in the specification, or a combination of them exists, and should be understood that it does not exclude the existence or possible addition of one or more other characteristics, numbers, steps, operations, elements, parts, or combinations of them in advance.

Furthermore, in this specification, if one element "transmits" data to the other element, this means that one element may directly transmit the data to the other element or may transmit the data to the other element through at least another element. In contrast, if one element "directly transmits" data to the other element, this means that the data is transmitted from one element to the other element without the intervention of another element.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

Hereinafter, the exemplary embodiments are described in detail reference to the accompanying drawings. The same reference numerals proposed in the drawings denote the same member.

FIG. 1 is a diagram illustrating a schematic system configuration of a disease diagnosis system using a neural network according to some exemplary embodiments.

Referring to FIG. 1, the disease diagnosis system using a neural network (hereinafter the diagnosis system 100) according to the exemplary embodiments is installed in a given server 10, and may implement the exemplary embodiments. The server 10 means a data processor having the operation ability for implementing the exemplary embodiments. In general, an average expert in the technical field of the exemplary embodiments may easily infer that not only a data processor accessible to a client over a network, but any device capable of performing a specific service, such as a personal computer or a mobile terminal, may be defined as the server.

Figure 3:
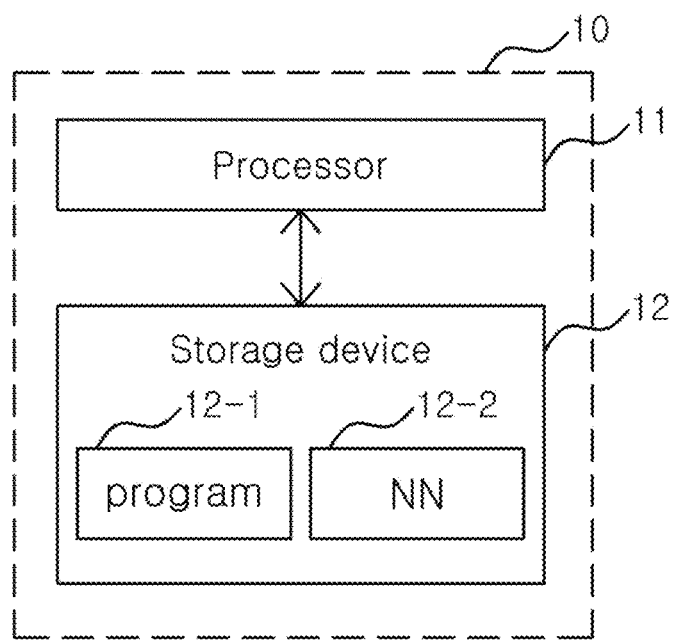
FIG. 3 is a diagram for describing a hardware configuration of the disease diagnosis system using a neural network according to an exemplary embodiment.

As illustrated in FIG. 3, the server 10 may include a processor 11 and a storage device 12. The processor 11 may mean an operation device capable of driving a program 12-1 for implementing the exemplary embodiments. The processor 11 may perform diagnosis using the program 12-1 and a neural network 12-2 defined by the exemplary embodiments. As will be described later, the neural network 12-2 may include a patch neural network that performs patch level diagnosis. According to an implementation example, the neural network 12-2 may further include a neural network that performs slide level diagnosis. According to exemplary embodiments, a configuration for performing the slide level diagnosis may be implemented through various machine learning schemes in addition to the neural network. According to the exemplary embodiments, known XGBoost has been used as a diagnosis engine that performs the slide level diagnosis, but diagnosis engines according to machine learning schemes using various methods may be implemented. Such a diagnosis engine may be stored in the storage device 12.

The storage device 12 may mean data storage means in which the program 12-1, the neural network 12-2 and/or the diagnosis engine performing slide level diagnosis may be stored. According to an implementation example, the storage device 12 may be implemented as a plurality of pieces of storage means. Furthermore, the storage device 12 may be a meaning including a temporary storage device or a memory which may be included in the processor 11, in addition to a main storage device included in the server 10.

The diagnosis system 100 has been illustrated as being implemented as any one physical device in FIG. 1 or 3, but an average expert in the technical field of the exemplary embodiments may easily infer that a plurality of physical device may be organically coupled to implement the diagnosis system 100 according to the exemplary embodiments, if preferable.

In this specification, when it is said that the diagnosis system 100 performs diagnosis, this may mean a series of processes of receiving a biometric image in which a biometric tissue is represented, that is, a patch, that is, the entire slide or some of a slide, and outputting output data defined in this specification.

According to an example, the diagnosis system 100 may perform two-phase diagnosis. The first phase may be a process of performing patch level diagnosis. In such a process, the diagnosis system 100 may receive an input for each patch of a slide, and may output whether a disease has been revealed in the corresponding patch. To this end, the neural network may be trained and implemented.

The second phase may output whether a disease has been revealed in the slide based on diagnosis results of the first phase. A neural network or a given machine learning schemes may be used for such a process.

That is, although a disease has been revealed in some patch based on diagnosis results for each patch, there may be a possibility that the disease is determined to have not been revealed in a biometric tissue corresponding to the entire slide including the corresponding patch. For example, a case where patches in which a disease is determined to have been revealed are excursively spread within a slide, a case where the number of patches is small, or other physical characteristics (e.g., a location, a size, and a degree of density) of patches in which disease is determined to have been revealed, such as the density, may have an important meaning in determining whether a disease has been actually revealed in a corresponding slide. Accordingly, the second phase can effectively perform diagnosis with high accuracy because whether a disease has been revealed in a slide is determined based on diagnosis results for each patch and characteristics of patches (i.e., patches in which a disease is diagnosed to have been revealed) determined based on the diagnosis results.

Meanwhile, according to the exemplary embodiments, the neural network that performs patch level diagnosis may perform diagnosis by further considering a surrounding patch of a corresponding patch, in addition to diagnosis using only the corresponding patch. Such information was specifically disclosed in a Korean Patent Application (a Korean Patent Application No. 10-2016-0168176, System and method for medical diagnosis using neural network, hereinafter referred to as "the prior application") filed by the present applicant. Accordingly, if even a surrounding region of a region corresponding to a patch is considered rather than performing diagnosis by considering only a very minor region, that is, the region corresponding to the patch, the accuracy of diagnosis can be further improved. Furthermore, according to the exemplary embodiments, there is an effect in that whether a disease is present in the entire slide can be more accurately determined by further considering physical characteristics, such as locations and density of patches and the size of a cluster, in the entire slide in addition to a surrounding patch of a specific patch. The prior application is included as a reference for the exemplary embodiments, and contents thereof may be treated as being written in this specification.

According to another embodiment of the exemplary embodiments, a micro-network and a macro-network, that is, a neural network using a two-way method is not used as in the prior application, but a single one-way neural network may be used. For example, a neural network according to an exemplary embodiment of the exemplary embodiments may be the same as that illustrated in FIG. 5.

In either case, the neural network has only to be a neural network defined to receive a patch and to output whether a disease has been revealed in the input patch. In this case, the neural network may be trained to further receive a gray channel as an input value in addition to original input values (e.g., RGB 3 channels) and to perform diagnosis.

Meanwhile, state information output by the neural network that performs patch level diagnosis may be information indicative of a probability that a specific disease (e.g., a specific type of cancer) has been revealed in a tissue corresponding to a patch. When a probability having a specific reference value (threshold value) or more appears, the neural network may determine the patch as a patch in which a disease (e.g., prostate cancer) has been revealed.

The state information output by the neural network may be information indicative of a progression of a specific disease (or a probability that will correspond to the progression) in addition to whether the specific disease has been revealed as disclosed in the prior application. For example, if the exemplary embodiments is used for diagnosis of prostate cancer, a Gleason pattern or a Gleason score, that is, an index indicative of a progression of prostate cancer, may be included in the state information output by the neural network. For example, the Gleason score has values 2 to 5, and indicates that a degree that prostate cancer has been revealed is severe as the value is increased. Accordingly, the state information may mean a probability that a biometric tissue corresponding to a patch, that is, a target for diagnosis, will correspond to a specific value (e.g., 3, 4, or 5) of the Gleason score.

The state information may be present in plural. For example, first state information may indicate a probability that the Gleason score will be 3, second state information may indicate a probability that the Gleason score will be 4, and third state information may indicate a probability that the Gleason score will be 5. All state channels corresponding to the first state information, the second state information, the third state information may be defined in is an output layer. According to an implementation example, state information indicative of a probability that the Gleason score will have a given range (e.g., 3 to 5, 4 to 5) may be defined. That is, one piece of state information may correspond to a plurality of indices that represents a progress state of a disease.

In such a case, when state information indicating that the Gleason score is 3 or more is a given threshold value or more, the neural network may determine a patch as a disease patch, that is, a patch in which a disease has been revealed.

Meanwhile, the threshold value used by the neural network may be variously set. According to an exemplary embodiment, a plurality of the threshold values may be used. A specific patch may be determined as a patch in which a disease has been revealed, that is, a disease patch, based on the threshold value, or may be determined as a normal patch according to the threshold values.

According to the exemplary embodiments, the threshold value used by the neural network may be plural. In such a case, disease patches diagnosed based on a plurality of threshold values, respectively, may be different. Accordingly, characteristics in which the disease patches are disposed in a slide may be different depending on the threshold values. Accordingly, if given threshold values are used, the accuracy of diagnosis results in a slide may also be different.

Accordingly, according to the exemplary embodiments, as will be described later, a slide diagnosis engine may be implemented to perform diagnosis on a slide by considering physical characteristics of disease patches diagnosed in the slide in multiple manners based on each of a plurality of threshold values, as described later.

If the diagnosis system 100 is included and implemented in the given server 10, the diagnosis system 100 may perform communication with at least one client (e.g., 20, 20-1) capable of accessing the server 10. In such a case, the client (e.g., 20, 20-1) may transmit a biometric image to the diagnosis system 100. The diagnosis system 100 may perform diagnosis according to the exemplary embodiments on the received biometric image. Furthermore, the diagnosis system 100 may transmit diagnosis results to the client (e.g., 20, 20-1).

The diagnosis system 100 may perform patch level diagnosis using a neural network according to the exemplary embodiments. In order to perform such diagnosis, the diagnosis system 100 may first perform a process of training the neural network. Furthermore, slide level diagnosis may also be performed using a given neural network as described above.

Accordingly, the diagnosis system 100 may be a system that receives a neural network trained according to the exemplary embodiments and a program for performing diagnosis using the neural network from the outside and performs diagnosis, and may be a system that performs even the training of a neural network. Furthermore, the diagnosis system 100 may be implemented as a dedicated device fabricated to implement the exemplary embodiments, not a general-purpose data processor. In such a case, the diagnosis system 100 may further include means for scanning a biometric image.

The neural network may have a characteristic in that it performs diagnosis on a specific patch by considering an image of at least one patch neighboring the specific patch in addition to an image of the specific patch itself, in order to perform diagnosis on the specific patch as disclosed in the prior application. There is an effect in that accuracy can be improved to a very meaningful level in the diagnosis of a disease in which even a state of a tissue around a biometric tissue corresponding to a specific patch needs to be actually considered in addition to the biometric tissue in order to diagnose the biometric tissue. Furthermore, if the biometric image is segmented into multiple patches, there is an effect that is robust against the influence of diagnosis results, which may occur depending on a method of segmenting a patch or a location of a biometric tissue where a segmented region is located.

As described above, the neural network may not have a characteristic disclosed in the prior application. In either case, the neural network may be a neural network trained to perform diagnosis for each patch.

In this case, unlike in a conventional technology, the neural network may further receive an additional channel as an input value with respect to each of pixels included in the patch. The additional channel may be a gray value of each pixel. Accordingly, the neural network may receive an input for each patch, and may further receive a gray channel, that is, an additional channel, along with original value (e.g., RGB) 3 channels of the pixels included in the patch.

In such a case, a robust effect can be obtained if a color of a biometric image may be changed by a factor (e.g., a characteristic or dyeing reagent of a diagnosis organ) not related to an image characteristic related to a disease. When an image characteristic related to a disease, which may occur if only a gray channel is used without simply using an original value, is incorporated and displayed in color, there is a problem in that such pieces of important information are not incorporated into learning. Such a problem can be solved.

Figure 2:
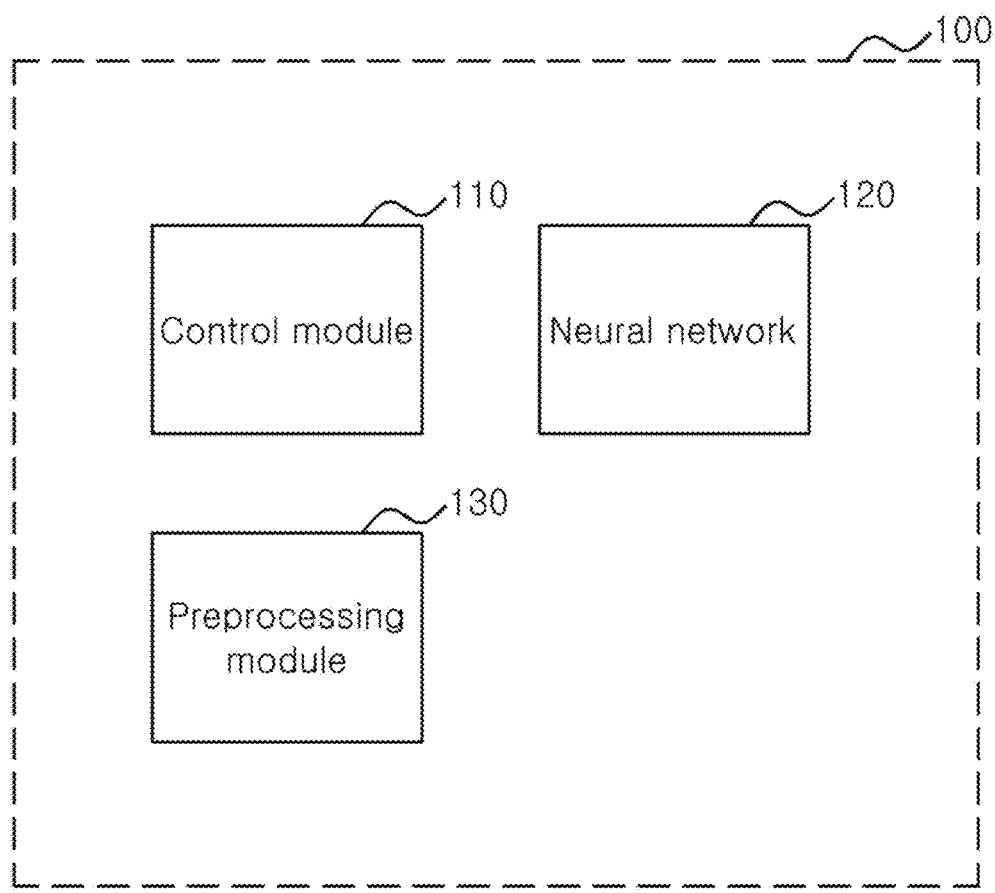
FIG. 2 is a diagram for describing a logical configuration of the disease diagnosis system using a neural network according to an exemplary embodiment.

The diagnosis system 100 for implementing may have a configuration such as FIG. 2.

FIG. 2 is a diagram for describing a logical configuration of the disease diagnosis system using a neural network according to the exemplary embodiments.

Referring to FIG. 2, the diagnosis system 100 includes a control module 110 and a diagnosis module 120 in which the neural network and/or the slide diagnosis engine are stored. Furthermore, the diagnosis system 100 may further include a preprocessing module 130.

The diagnosis system 100 may mean a logical configuration including a hardware resource and/or software preferable to implement the exemplary embodiments, and does not essentially mean one physical element one device. That is, the diagnosis system 100 may mean a logical combination of hardware and/or software provided to implement the exemplary embodiments. The diagnosis system 100 may be implemented as a set of logical elements installed on isolated devices, respectively, if preferable, and for implementing the exemplary embodiments by performing respective functions. Furthermore, the diagnosis system 100 may mean a set of elements separately implemented for respective functions or roles for implementing the exemplary embodiments. For example, the control module 110, the diagnosis module 120 and/or the preprocessing module 130 may be located in different physical devices or may be located in the same physical device. Furthermore, according to an implementation example, a combination of software and/or hardware that constitute the control module 110, the diagnosis module 120 and/or the preprocessing module 130 may be located in different physical devices, and elements located in different physical devices may be organically combined to implement each of the modules.

Furthermore, in this specification, the module may mean a functional, structural combination of hardware for performing the exemplary embodiments and software for driving the hardware. For example, the module may mean a logical unit of a given code and a hardware resource by which the given code is performed. An average expert in the technical field of the exemplary embodiments may easily infer that the module does not essentially mean a physically connected code or one type of hardware.

The control module 110 may control another element (e.g., the diagnosis module 120 and/or the preprocessing module 130) included in the diagnosis system 100 in order to implement the exemplary embodiments.

Furthermore, the control module 110 may perform diagnosis according to the exemplary embodiments using the neural network and/or the slide diagnosis engine stored in the diagnosis module 120.

The diagnosis module 120 may include a patch diagnosis engine for performing patch level diagnosis and the slide diagnosis engine for performing slide level diagnosis.

As described above, the patch level diagnosis engine may be implemented through the neural network based on deep learning according to the exemplary embodiments. The neural network based on deep learning may be used for the slide diagnosis engine, and a given machine learning (e.g., XGBoost) engine not the neural network may be used for the slide diagnosis engine.

The neural network may mean a set of information that represents a series of design factors to define the neural network. In this specification, the neural network may be a convolutional neural network.

As well known, the convolutional neural network may include an input layer, a plurality of hidden layers, and an output layer. Each of the plurality of hidden layers may include a convolution layer and a pooling layer (or subsampling layer).

The convolutional neural network may be defined by a function, a filter, a stride, a wait factor, etc. for defining each of such layers. Furthermore, the output layer may be defined by a fully connected forward layer (FeedForward layer).

Design factors for each layer that constitute the convolutional neural network are widely known. For example, known functions may be used for the number of layers to be included in a plurality of layers, a convolution function for defining the plurality of layers, a pooling function, and an activation function. Functions separately defined in order to implement the exemplary embodiments may be used.

According to the exemplary embodiments, the neural network performing patch level diagnosis uses a known DenseNet. In this case, as disclosed in the prior application, the neural network may be designed to consider even a surrounding patch in addition to a specific patch, that is, a target for diagnosis. In addition, various neural networks may be used. In either case, the neural network may be defined to receive a specific patch and to output a feature value corresponding to a probability that a disease has been revealed in the corresponding specific patch.

The control module 110 may receive input data, that is, an input for each patch to the neural network stored in the diagnosis module 120, that is, a trained neural network. In this case, as described above, the control module 110 may receive a value in which a gray channel value has been added to an original value. The gray channel value may be obtained by converting a pixel value into a gray value. Furthermore, the control module 110 may output output data, that is, a feature value corresponding to a disease revelation probability corresponding to a patch. Furthermore, according to the exemplary embodiments, for slide level diagnosis to be described later, the control module 110 may output whether a disease has been revealed in a corresponding patch depending on whether a feature value is a given threshold value or more.

Furthermore, the diagnosis module 120 may include the slide diagnosis engine. The slide diagnosis engine may be trained and implemented by the control module 110.

The slide diagnosis engine may mark a disease patch based on output results of the neural network. The marking may mean that disease patches are classified within a slide. According to an example, the slide diagnosis engine may generate a heatmap by indicating disease patches to be different from another patch. Furthermore, the slide diagnosis engine may cluster the disease patches in plural based on the generated heatmap. According to an exemplary embodiment, the slide diagnosis engine may cluster the disease patches into at least two. Furthermore, the slide diagnosis engine may use the greatest two clusters of the clusters for slide diagnosis. However, the slide diagnosis engine may use two or more clusters for slide diagnosis.

The slide diagnosis engine may calculate a given feature value for each cluster. Furthermore, the slide diagnosis engine is trained to output whether a disease has been revealed in a slide corresponding to received input data by using the calculated feature value as input data.

Furthermore, the slide diagnosis engine may be trained by considering all of a plurality of threshold values. Accordingly, the slide diagnosis engine may output a slide diagnosis result robust against the setting of a threshold value. This is described later.

The preprocessing module 130 may perform preprocessing on a required biometric image before performing diagnosis using the neural network. For example, the preprocessing for the biometric image may include a process of patching the biometric image into patches having a predefined size. As described above, the preprocessing module may calculate a gray value of pixels for each patch. Furthermore, an average expert in the technical field of the exemplary embodiments may easily infer that the preprocessing module can perform proper image processing using a method suitable for the neural network, if preferable.

FIG. 4 is a diagram for describing an exemplary configuration of a neural network according to the exemplary embodiments.

Referring to FIG. 4, the neural network 200 according to the exemplary embodiments includes a micro-neural network and a macro-neural network.

Figure 4A:
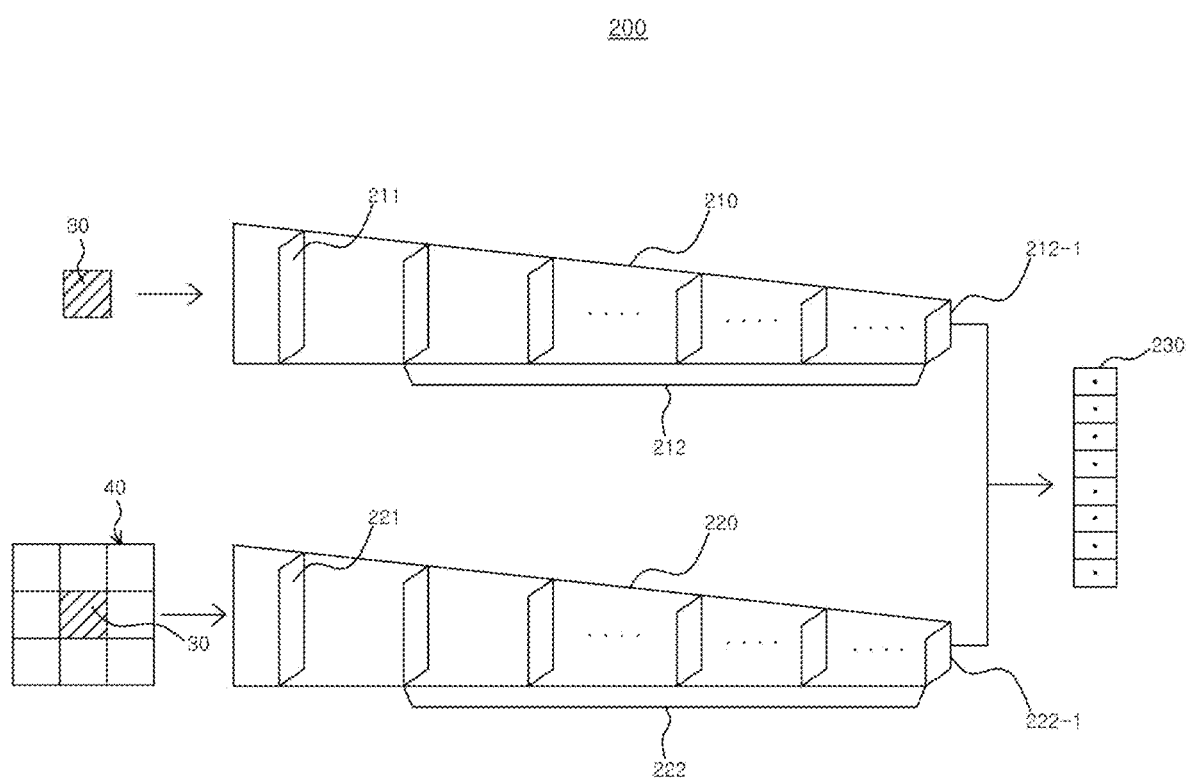
FIG. 4A and FIG. 4B are diagrams for describing an exemplary configuration of a neural network according to an exemplary embodiment.

Referring first to FIG. 4a, as disclosed in the prior application, the micro-neural network includes a plurality of layers 210 and an output layer 230. The plurality of layers 210 includes an input layer 211 and a plurality of hidden layers 212.

The macro-neural network includes a plurality of layers 220 and the output layer 230. The plurality of layers 220 includes an input layer 221 and a plurality of hidden layers 222.

The micro-neural network is defined to receive a specific patch 30 and to output diagnosis results of the specific patch, that is, output data defined in the output layer 230.

Furthermore, the macro-neural network is defined to receive a macro-patch 40 including the specific patch 30 and including at least one patch neighboring the specific patch 30 and to output diagnosis results of the specific patch.

That is, the neural network 200 according to the exemplary embodiments may output the diagnosis results of the specific patch 30 by considering image characteristic of patches neighboring the specific patch 30 in addition to image characteristics of the specific patch 30 in order to output the diagnosis results of the specific patch 30.

An example in which 3×3 patches surrounding the patch are used as the macro-patch 40 is illustrated in FIG. 4, but the macro-patch 40 may include various exemplary embodiments.

The output layer 230 may receive output data of a first previous layer 212-1, that is, a layer previous to the output layer 230 included in the micro-neural network, and output data of a second previous layer 222-1, that is, a layer previous to the output layer 230 included in the macro-neural network, and may produce output data defined in the output layer 230. The first previous layer 212-1, the second previous layer 222-1, and the output layer 230 may be fully connected.

Any one of various functions for outputting output data to the output layer 230 as results through the neural network 200 using input data input to the input layer may be used as a feed-forward function to define the output layer 230.

As a result, the neural network 200 is trained to output the output data of the output layer 230 corresponding to an annotation value of multiple training data by considering image characteristics of the specific patch 30 and image characteristics of the macro-patch 40, including the specific patch 30, together in order to perform diagnosis on the specific patch 30.

That is, multiple training data is used to train the neural network 200. The multiple training data may include a pair of the specific patch 30 and the macro-patch 40. Furthermore, training may also be performed on the macro-patch 40 using annotation information of the specific patch 30.

Accordingly, the neural network 200 may be trained to produce output data, corresponding to the annotation information of the specific patch 30, by considering all of the image characteristics of the specific patch 30 and the macro-patch 40.

Furthermore, when receiving a target patch, that is, a target for diagnosis, and a macro-patch corresponding to the target patch, as input data of the input layers of the micro-neural network and the macro-neural network, the trained neural network 200 may output diagnosis results of the target patch, that is, output data of the output layer 230.

As illustrated in FIG. 4a, the output layer 230 may output, as output data, diagnosis results for the specific patch 30, that is, a target for diagnosis. The diagnosis results may include at least information on a state of a disease in the specific patch 30. The information on a state of a disease may simply mean information on whether a specific disease has been revealed in the specific patch 30 (or a probability value). However, more specifically, the information on a state of a disease may include information indicative of a progression of a disease depending on the type of disease.

As disclosed in the prior application, the output layer may be designed to output several pieces of additional information, in addition to simply outputting whether a disease has been revealed. For example, the several pieces of additional information may include information indicative of a progression of a disease and/or association factor information indicative of a revelation degree of an association factor associated with a value of the state channel. This has been specifically disclosed in the prior application, and thus a detailed description thereof is omitted.

If the neural network 200 illustrated in FIG. 4a is used, although not illustrated in FIG. 4a, a layer that receives output data of the output layer 230 and outputs a feature value corresponding to a probability that a disease has been revealed in a finally input patch may be further present.

Figure 4B:
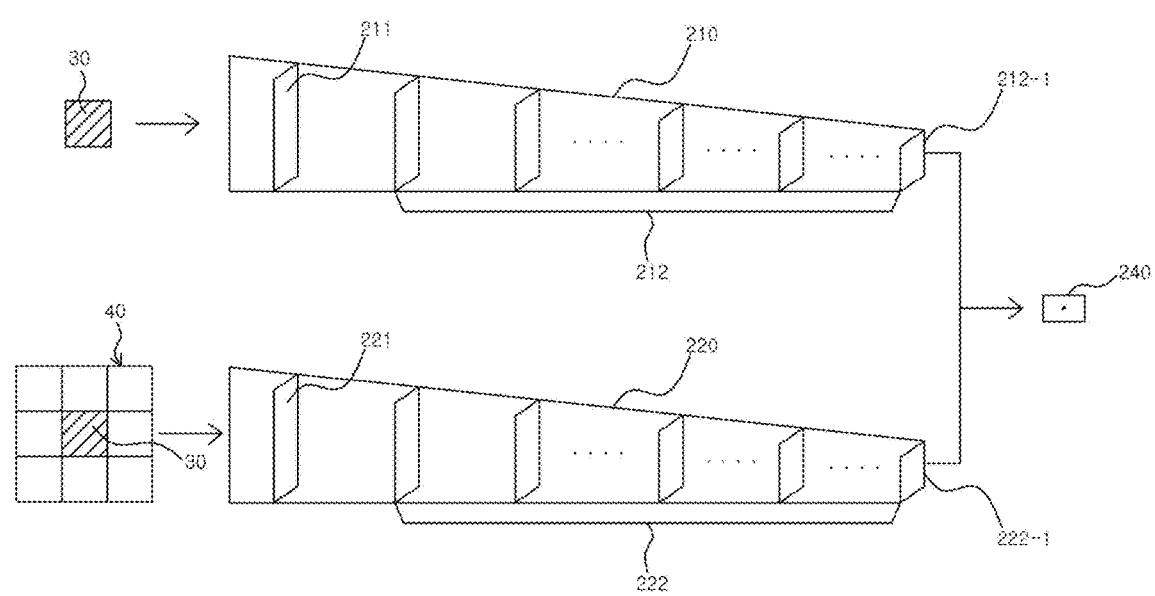

Alternatively, as illustrated in FIG. 4b, the neural network may be designed to include a layer 240 that outputs a feature value corresponding to a probability that a disease has been revealed in an input patch, instead of the layer that outputs a plurality of state channels and an association factor channel as illustrated in FIG. 4a.

According to another exemplary embodiment, as illustrated in FIG. 4, the neural network for patch level diagnosis may be designed to have a single path, not a method having two paths (paths for the micro-network and the macro-network, respectively). Such an example may be the same as that illustrated in FIG. 5.

Figure 5:
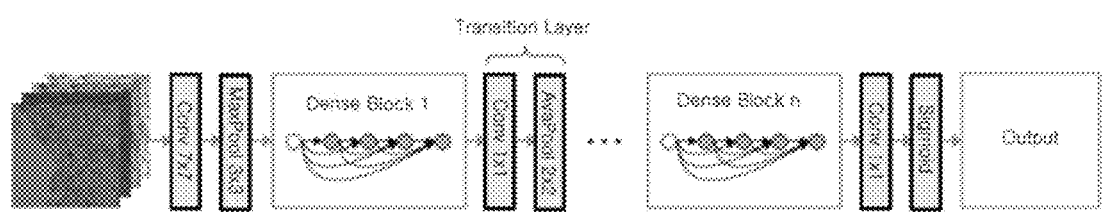
FIG. 5 is a diagram for describing an exemplary configuration of a neural network according to another exemplary embodiment.

FIG. 5 is a diagram for describing an exemplary configuration of a neural network according to the exemplary embodiments.

Referring to FIG. 5, as described above, the neural network may be defined to receive an input in a patch unit and to determine whether a disease is present in the input patch. In this case, as illustrated, the neural network may receive 4-channel (e.g., RGB and Gray channel) data.

As illustrated in FIG. 5, input data may be defined to be output as output data, that is, whether an input patch is a disease patch through multiple layers include convolution layer or max pooling etc. Such a neural network may be a neural network using a known DenseNet model. Furthermore, in this case, it may be seen that an original DenseNet model versus 1×1 convolution is added to the neural network according to the exemplary embodiments. Accordingly, there is an effect in that an internal feature map can be seen. Furthermore, a sigmoid function is used as an active function, and various active functions may be used.

An average expert in the technical field of the exemplary embodiments may easily infer that a neural network performing patch level diagnosis in various other methods may be defined.

According to an exemplary embodiment, the neural network illustrated in FIG. 5 is used. In this case, the patch level diagnosis results of the neural network may be the same as those illustrated in FIG. 7.

Figures 6, 7:
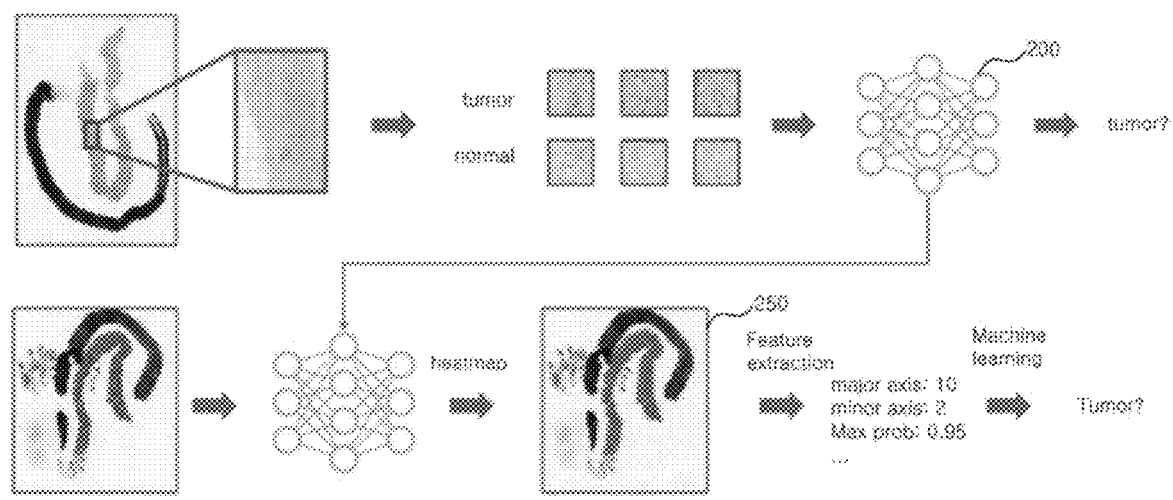
FIG. 6 is a diagram for describing a concept of a two-phase disease diagnosis method according to an exemplary embodiment.
FIG. 7 is a diagram illustrating experiment results of a patch level diagnosis method according to an exemplary embodiment.

FIG. 7 is a diagram illustrating experiment results of a patch level diagnosis method according to an exemplary embodiment.

Referring to FIG. 7, the neural network was trained by 62358 patches labeled as cancer and 108300 patches labeled as a normal, as a train data set. 8963 patches, that is, cancer, and 15499 patches, that is, a normal, were used as a validation set. Furthermore, 14898 patches, that is, cancer, and 19089 patches, that is, a normal, were used as a test set.

Furthermore, as illustrated in FIG. 6, it could be seen that accuracy, precision, sensitivity, and specificity, that is, experiment results at that time, showed very high performance. Furthermore, it was found that performance was improved compared to a case where only three channels were used for pixel values original values.

The concept of two-phase diagnosis using such patch level diagnosis results is described with reference to FIG. 6.

FIG. 6 is a diagram for describing the concept of the two-phase disease diagnosis method according to the exemplary embodiments.

As illustrated in FIG. 6, a biometric image corresponding to a biometric tissue, that is, patches sampled from a slide, may be used to train the neural network 200. The patches may have been sampled to have a given ratio of patches labeled as cancer and patches labeled as a normal.

Furthermore, as described above, the neural network 200 is trained to receive input data for each patch further including a gray channel. As a result, the neural network 200 is trained to output whether each patch is cancer (or a probability value).

Accordingly, as described above, as illustrated on the lower side of FIG. 6, when receiving a slide, the trained neural network 200 may perform patch level diagnosis on each of patches included in each slide.

Furthermore, the slide diagnosis engine may mark a disease patch based on the patch level diagnosis results. For example, as illustrated in FIG. 6, the slide diagnosis engine may generate a heatmap.

Figure 8A:
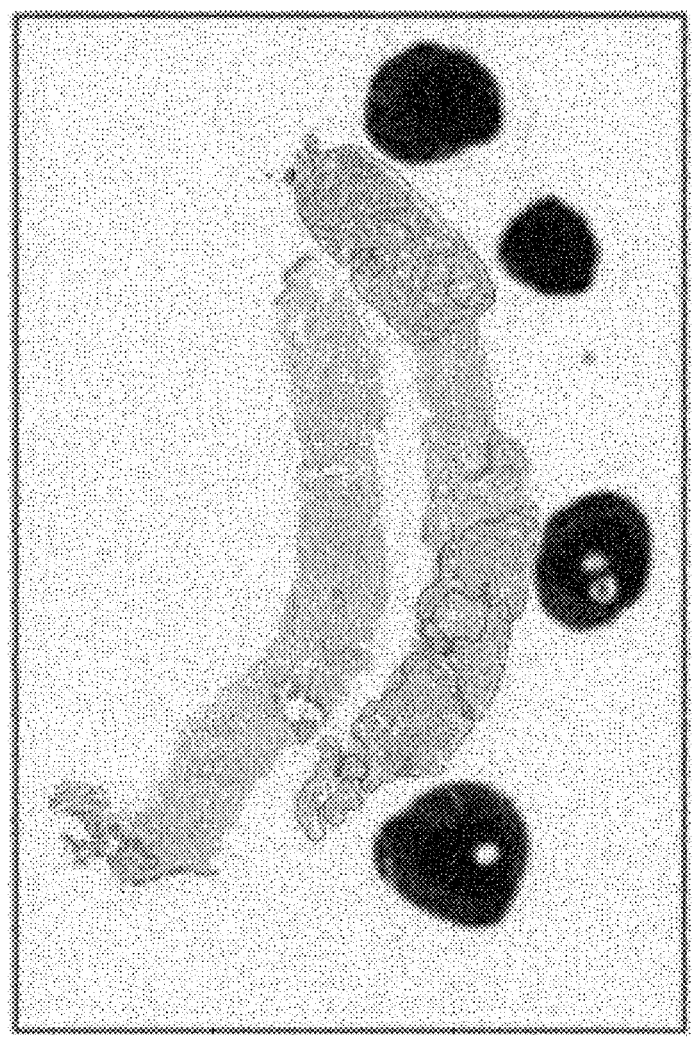
FIG. 8A and FIG. 8B are diagrams illustrating marking results according to patch level diagnosis results according to an exemplary embodiment.
Figure 8B:
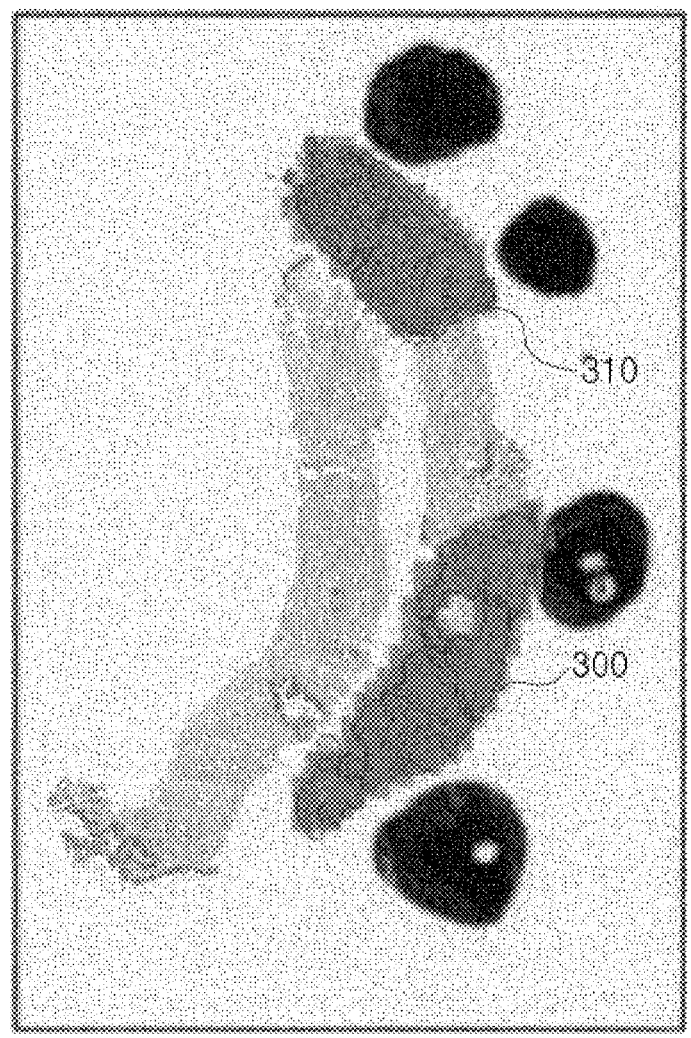

Furthermore, FIG. 8 is a diagram illustrating marking results according to the patch level diagnosis results according to the exemplary embodiments. FIG. 8a illustrates an image of a biometric tissue labeled by an experienced expert. FIG. 8b illustrates a heatmap generated by the trained neural network 200. From FIG. 8, it may be seen that very accurate diagnosis may be possible.

Meanwhile, the slide diagnosis engine may generate a cluster based on the generated heatmap. The slide diagnosis engine may cluster disease patches using a given clustering algorithm. According to the exemplary embodiments, the slide diagnosis engine was performed the clustering using a known DB SCAN algorithm, but various clustering schemes may be used.

The slide diagnosis engine may extract a cluster feature for each cluster generated as a result of the clustering.

The cluster feature may be a characteristic value which may indicate a characteristic associated with the revelation of a disease.

According to an example, the cluster feature may include the number of disease patches included in a cluster, an average of probability values for a possible disease for each patch, a maximum value of probability values for a possible disease for each patch, and a minimum value of probability values for a possible disease for each patch. If such a cluster feature is included, it could be seen that diagnosis results of the slide diagnosis engine are relatively increased.

Furthermore, according to exemplary embodiments, the cluster feature may further include a major axis, a minor axis, an area, and density of each cluster. The cluster feature is closely associated with a physical characteristic of a cluster. If such a cluster feature is used together, diagnosis performance can be further improved.

Meanwhile, the location, size and cluster feature of the cluster may be different depending on whether each patch is determined as a disease patch. Furthermore, this depends on which threshold value is used in patch level diagnosis.

According to the exemplary embodiments, a plurality of threshold values may be together used for slide level diagnosis.

According to an example, in an exemplary embodiment, five different threshold values were used, but various embodiments may be possible.

Furthermore, the results of a specific patch diagnosed as a disease patch may be different depending on each threshold values. Accordingly, clustering results may be different.

The slide diagnosis engine according to the exemplary embodiments formed M (e.g., 2) clusters by clustering N (e.g., 5) threshold values and a patch in which a disease has been revealed based on each of the N threshold values, for example, using a given method.

Furthermore, P (e.g., the aforementioned 8 cluster features) cluster features were calculated for each of the formed clusters. Furthermore, in such a case, M×N×P (e.g., 80) cluster features may be extracted for one slide.

Furthermore, the slide diagnosis engine may be trained to receive such feature values as an input value and to output whether a disease is present in a slide as output data.

Experiment results through such an embodiment are illustrated in FIG. 9.

FIG. 9 is a diagram illustrating experiment results of a slide level diagnosis method according to the exemplary embodiments.

The experiment results illustrated in FIG. 9 illustrate experiment results in which all of the eight cluster features were used, five threshold values were used, and two clusters are used. In such an exemplary embodiment, 478 slides in which cancer was revealed and 218 slides, that is, a normal, were used as a train data set. Furthermore, 117 slides in which cancer was revealed and 57 slides, that is, a normal, were used as a validation set. 1302 slides in which cancer was revealed and 1658 slides, that is, a normal, were used as a test set.

Furthermore, it could be seen that accuracy, precision, sensitivity, and specificity, that is, experiment results at that time, showed high performance as illustrated in FIG. 9.

Furthermore, in this specification, an example in which the exemplary embodiments has been applied to prostate cancer has been chiefly described. However, an average expert in the technical field of the exemplary embodiments may easily infer that accurate diagnosis may be possible if the exemplary embodiments is applied to another disease on which diagnosis for a specific tissue needs to be performed by considering a state of a tissue around the corresponding tissue in addition to the specific tissue.

The two-phase disease diagnosis method according to the exemplary embodiments may be implemented in a computer-readable recording medium in the form of computer-readable code. The computer-readable recording medium includes all types of recording devices in which data readable by a computer system is stored. Examples of the computer-readable recording medium may include a ROM, a RAM, a CD-ROM, magnetic tapes, floppy disks, and optical data storages. Furthermore, the computer-readable recording medium may be distributed to computer systems connected over a network, and may have a computer-readable code stored and executed in a distributed manner. Furthermore, a functional program, a code and code segments for implementing the exemplary embodiments may be easily reasoned by programmers of the technical field to which the exemplary embodiments pertains.

The exemplary embodiments may be used in a "two-phase disease diagnosis system and a method thereof."

Although certain exemplary embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

The invention claimed is:

1. A two-phase disease diagnosis system, comprising a processor and a storage device storing a neural network, and using a slide comprising a biometric image and the neural network, the system comprising:
a patch neural network that receives, through an input layer, a given patch segmented in a given size from the slide and outputs patch level diagnosis results indicating whether a disease is present in the patch; and
a slide diagnosis engine that marks a patch determined to be cancer based on the patch level diagnosis results for each of multiple patches included in the slide and outputs slide level diagnosis results indicating whether a disease is present in the slide based on the marked results,
wherein:
the patch neural network comprises a layer which outputs a feature value corresponding to a probability that a disease is to have been revealed in the patch; and
the patch neural network outputs patch level diagnosis results in which a corresponding patch is determined to be cancer when a feature value is a given threshold value or more, and outputs a plurality of patch level diagnosis results for one patch based on each of a plurality of the threshold values.

2. The two-phase disease diagnosis system of claim 1, wherein the slide diagnosis engine forms a plurality of clusters by clustering patches determined to be cancer using a given method,
receives a plurality of cluster features of each of the formed clusters as an input value, and
outputs the slide level diagnosis results for the slide comprising the clusters.

3. The two-phase disease diagnosis system of claim 1, wherein the slide diagnosis engine
forms M (M is a natural number equal to or greater than 2) clusters by clustering N (N is a natural number equal to or greater than 2) threshold values and a patch in which a disease has been revealed based on each of the N threshold values using a given method,
calculates P (P is a natural number equal to or greater than 2) cluster features for each of the formed clusters,
receives M×N×P cluster features as at least a value, and
outputs the slide level diagnosis results for the slide comprising the clusters.

4. The two-phase disease diagnosis system of claim 1, wherein the cluster feature comprises a number of patches, an average of probability values for a possible disease for each patch, a maximum value of probability values for a possible disease for each patch, and a minimum value of probability values for a possible disease for each patch.

5. The two-phase disease diagnosis system of claim 4, wherein the cluster feature further comprises a major axis, a minor axis, an area, and density of each of the clusters.

6. The two-phase disease diagnosis system of claim 1, wherein the disease is prostate cancer.

7. A two-phase disease diagnosis system implemented in a system, comprising a processor and a storage device storing a neural network, and using a slide which is a biometric image and the neural network, the diagnosis system comprising:
a patch neural network that receives, through an input layer, a given patch segmented in a given size from the slide and outputs patch level diagnosis results indicating whether a disease is present in the patch; and
a slide diagnosis engine that marks a patch determined to be cancer based on the patch level diagnosis results for each of multiple patches included in the slide and outputs slide level diagnosis results indicating whether a disease is present in the slide based on the marked results,
wherein the slide diagnosis engine forms a plurality of clusters by clustering patches determined to be cancer using a given method, receives a plurality of cluster features of each of the formed clusters as an input value, and outputs the slide level diagnosis results for the slide comprising the clusters.

8. A disease diagnosis method implemented in a system, comprising a processor and a storage device storing a neural network, and using a slide which is a biometric image and the neural network, the method comprising steps of:
receiving, by the system, a given patch segmented in a given size from the slide through an input layer and outputting patch level diagnosis results indicating whether a disease is present in the patch; and
marking, by the system, a patch determined to be cancer based on the patch level diagnosis results for each of multiple patches included in the slide and outputs slide level diagnosis results indicating whether a disease is present in the slide based on the marked results,
the step of outputting the slide level diagnosis results comprises steps of:
forming, by the system, a plurality of clusters by clustering patches determined to be cancer using a given method; and
receiving a plurality of cluster features of each of the formed clusters as an input value and outputting the slide level diagnosis results for the slide comprising the clusters.

9. The method of claim 8, wherein the step of outputting the patch level diagnosis results further comprises:
the neural network comprising a layer which outputs a feature value corresponding to a probability that a disease is to have been revealed in the patch, and
a step of outputting patch level diagnosis results for determining a corresponding patch to be cancer when a feature value is a given threshold value or more,
wherein a plurality of patch level diagnosis results for one patch is output based on each of a plurality of the threshold values.

10. The method of claim 9, wherein the step of outputting the slide level diagnosis results comprises steps of:
forming M (M is a natural number equal to or greater than 2) clusters by clustering N (N is a natural equal to or greater than 2) threshold values and a patch for a revealed disease based on each of the N threshold values using a given method; and
calculating P (P is a natural number equal to or greater than 2) cluster features for each of the formed clusters, receiving M×N×P cluster features as at least a value, and outputting the slide level diagnosis results for the slide comprising the clusters.

11. A computer program installed in a data processor and written in a medium for performing the method according to claim 8.

12. A disease diagnosis method implemented in a system, comprising a processor and a storage device storing a neural network, and using a slide comprising a biometric image and the neural network, the method comprising steps of:

receiving, by the system, a given patch segmented in a given size from the slide through an input layer and outputting patch level diagnosis results indicating whether a disease is present in the patch; and marking, by the system, a patch determined to be cancer based on the patch level diagnosis results for each of multiple patches included in the slide and outputs slide level diagnosis results indicating whether a disease is present in the slide based on the marked results, wherein the step of outputting the slide level diagnosis results comprises a step of forming a plurality of clusters by clustering patches determined to be cancer using a given method, receiving a plurality of cluster features of each of the formed clusters as an input value, and outputting the slide level diagnosis results for the slide comprising the clusters.

* * * * *